United States Patent
Kapelke (10) Patent No.: US 8,192,501 B2
(45) Date of Patent: Jun. 5, 2012

(54) PROSTHETIC KNEE WITH GRAVITY-ACTIVATED LOCK

(75) Inventor: Peter Kapelke, Salt Lake City, UT (US)

(73) Assignee: Shriners Hospital for Children, Tampa, FL (US)

(*) Notice: Subject to any disclaimer, the term of this patent is extended or adjusted under 35 U.S.C. 154(b) by 392 days.

(21) Appl. No.: 12/567,301

(22) Filed: Sep. 25, 2009

(65) Prior Publication Data

US 2010/0082115 A1    Apr. 1, 2010

Related U.S. Application Data

(60) Provisional application No. 61/100,852, filed on Sep. 29, 2008.

(51) Int. Cl.
*A61F 2/64* (2006.01)
*A61F 2/70* (2006.01)
(52) U.S. Cl. ............................. 623/24; 623/44
(58) Field of Classification Search ........................ None
See application file for complete search history.

(56) References Cited

U.S. PATENT DOCUMENTS

| 2,561,370 A | 7/1951 | Henschke et al. |
| 3,683,423 A | 8/1972 | Crapanzano |
| 4,685,926 A * | 8/1987 | Haupt ............................. 623/43 |

FOREIGN PATENT DOCUMENTS

| EP | 0 141 640 A | 5/1985 |
| GB | 2 099 708 A * | 12/1982 |

* cited by examiner

*Primary Examiner* — David H. Willse
(74) *Attorney, Agent, or Firm* — Saliwanchik, Lloyd & Eisenschenk (57) ABSTRACT

Disclosed is a prosthetic knee appliance having upper and lower leg elements with a single-axis, articulating joint therebetween controllable with an electric knee-lock mechanism. A tilt-switch located within the prosthetic knee can facilitate activation of the electric knee-lock to lock or unlock the joint when the lower leg element is in a pre-determined position. A remote control can provide external locking control of the articulating joint. A pressure switch can ensure that the free-knee is locked only when the lower leg element is sufficiently extended relative to the upper leg element. The mobility of a free-knee system combined with the stability of a straight-leg prosthesis can be advantageous for pre-ambulatory pediatric patients.

15 Claims, 6 Drawing Sheets

PROSTHETIC KNEE WITH GRAVITY-ACTIVATED LOCK

CROSS-REFERENCE TO A RELATED APPLICATION

This application claims the benefit of U.S. provisional application Ser. No. 61/100,852 filed Sep. 29, 2008, which is incorporated herein by reference in its entirety.

BACKGROUND OF INVENTION

Prosthetic knee appliances have evolved over the past decades into highly complex technical components. The evolution of prosthetic knee systems has resulted in numerous choices being available to patients, doctors, and prosthetists. The use of almost any prosthetic knee system requires that patients learn and develop skills to control the motion of the joint so that they can walk, stand, sit, and generally maintain stability. Therefore, when selecting a prosthetic knee system, a variety of factors must be considered, such as the patient's age, health, activity level, and lifestyle.

The use of prosthetic knee systems by very young children can be particularly problematic. Never more so than with infants and children who have not yet learned to walk. Traditionally, infants and pre-ambulatory children who have undergone trans-femoral (above-knee) or knee-disarticulation (at the knee) amputation are initially fitted with pediatric straight leg prostheses. This ensures knee stability in early "cruising" (walking sideways while holding onto furniture or other supports) and walking stages. However, straight-leg prostheses can dramatically inhibit normal crawling and other movements in these young patients.

The use of an articulated or "free-knee" prosthetic eases crawling and allows for normal body positioning and movement while sitting. For children learning to walk, a free-knee prosthetic also aids in the initial step of pulling to a standing position. But, ambulation requires a stabile knee. In order for a traditional free-knee prosthetic to remain straight during weight bearing, the center of mass must be in front of the knee or there must be hip extensor movement keeping the knee locked. This is a learned skill that cannot be expected of a child just learning to walk. Inevitably, as a child takes his or her first steps and transfers weight to the prosthesis, the center of mass collapses behind the axis of the free-knee joint causing the child to fall.

Despite advances in prosthetic knee devices, there still exists a need for a pediatric prosthetic knee system that provides the advantages of free-knee movement and the security of a straight knee for standing and ambulation. Such a prosthetic knee system would aid in the proper movement and development of pre-ambulatory pediatric patients.

BRIEF SUMMARY

The subject invention pertains to an advantageous prosthetic knee system that enables free-knee movement, but includes a locking mechanism that can secure the knee joint at appropriate times.

Free-knee prosthetic systems provide patients with increased flexibility, such as that required for sitting. This can be particularly important for pediatric patients that are pre-ambulatory and still in the crawling and/or "scooting" stage of development.

The use of the free-knee prosthesis of the subject invention encourages normal movement and development in children. Advantageously, the prosthesis of the subject invention has the ability to lock when the knee is sufficiently vertically aligned, such as when the patient reaches a standing position.

Young children learning to walk will usually pull themselves to a standing position before they take a step. With the locking prosthetic knee device of the subject invention, a child can pull up to a standing position and learn to walk in a relatively normal fashion.

In a preferred embodiment, the prosthetic knee system of the subject inventions employs a single-axis externally mounted joint for use by trans-femoral or knee-disarticulation amputees. The locking mechanism, when activated, prevents rotation of the joint elements. A sensor can also be utilized to prevent the lock from engaging if the joint elements are not sufficiently extended or vertically-aligned. Further, the locking mechanism of the subject invention can have internal mechanism(s) that automatically engage when the prosthetic elements are properly positioned or which can be controlled externally.

BRIEF DESCRIPTION OF DRAWINGS

In order that a more precise understanding of the subject invention be obtained, a more particular description of the invention briefly described above will be rendered by reference to specific embodiments thereof that are illustrated in the appended drawings. Understanding that these drawings depict only typical embodiments of the invention and are not therefore to be considered as limiting in scope, the invention will be described and explained with additional specificity and detail through the use of the accompanying drawings in which.

DETAILED DISCLOSURE

The subject invention provides prosthetic free-knee systems. More specifically, the subject invention pertains to embodiments of prosthetic knee systems that can be locked into a straightened or extended position.

The subject invention is particularly useful for pre-ambulatory pediatric patients. However, a person with skill in the art and having benefit of the subject disclosure will recognize that other types of patients can benefit from the disclosed devices and methods. Thus, uses with other than pediatric patients and any modification(s) required therefor, not inconsistent with the teachings of the subject application, are contemplated to be within the scope of the present invention.

As used herein, the terms "front", "forward", "back" or "backward", with reference to motion of the subject invention, are relative to the front (facing) and rear (posterior) of a patient. Thus, for example, reference to motion in the "forward" direction pertains to the front of a patient that may be wearing a prosthetic device of the subject invention.

As used herein, and unless otherwise specifically stated, the terms "operable communication" and "operably connected" mean that the particular elements are connected in such a way that they cooperate to achieve their intended function or functions. The "connection" may be direct, or indirect, physical or remote.

The present invention is more particularly described in the following examples that are intended to be illustrative only, since numerous modifications and variations therein will be apparent to those skilled in the art. It should also be understood that as used in the specification and in the claims, the singular for "a," "an" and "the" include plural referents unless the context clearly dictates otherwise.

With reference to the attached figures, it can be seen that the subject invention comprises an upper leg element 20 and a lower leg element 40 with a single-axis articulating joint 60 therebetween. The upper leg element 20 can include a receptacle 22 for the residual limb. The lower leg element can include a fixed or a moveable prosthetic foot 41. The upper leg element and the lower leg element are fixedly connected to the articulating joint 60 by the use of an upper rod 24 and a lower rod 43, respectively. The length of the upper rod 24 and lower rod 43 can vary depending upon the dimensions of the leg elements used. In a further embodiment, the upper rod 24 and lower rod 43 are removable from the articulating joint. In a specific embodiment, the upper and lower rods comprise an appropriately rigid material, such as, for example, metals, plastics, wood, ceramics, rubber, and/or other appropriate materials or combinations thereof As will be described herein, a locking mechanism 30 can be employed to control the motion of the articulating joint 60.

In one embodiment, the single-axis articulating joint 60 permits motion of the lower leg element 40, relative to the upper leg element 20, that is the same or similar to that of a natural leg. In this embodiment, the articulating joint 60 works in similar fashion to a human knee. The lower leg element can move backwards to a fully articulated position that is generally perpendicular to the upper leg element, but forward motion is restricted beyond the extended position, where the upper and lower leg elements are substantially aligned. In one embodiment, the articulating joint 60 works like a one-way hinge or folding joint. In this embodiment, the single-axis rotating element 63 allows motion of the lower leg element in the desired backward direction and a stop flange 65 restricts motion in the opposite or forward direction.

Figure 1:
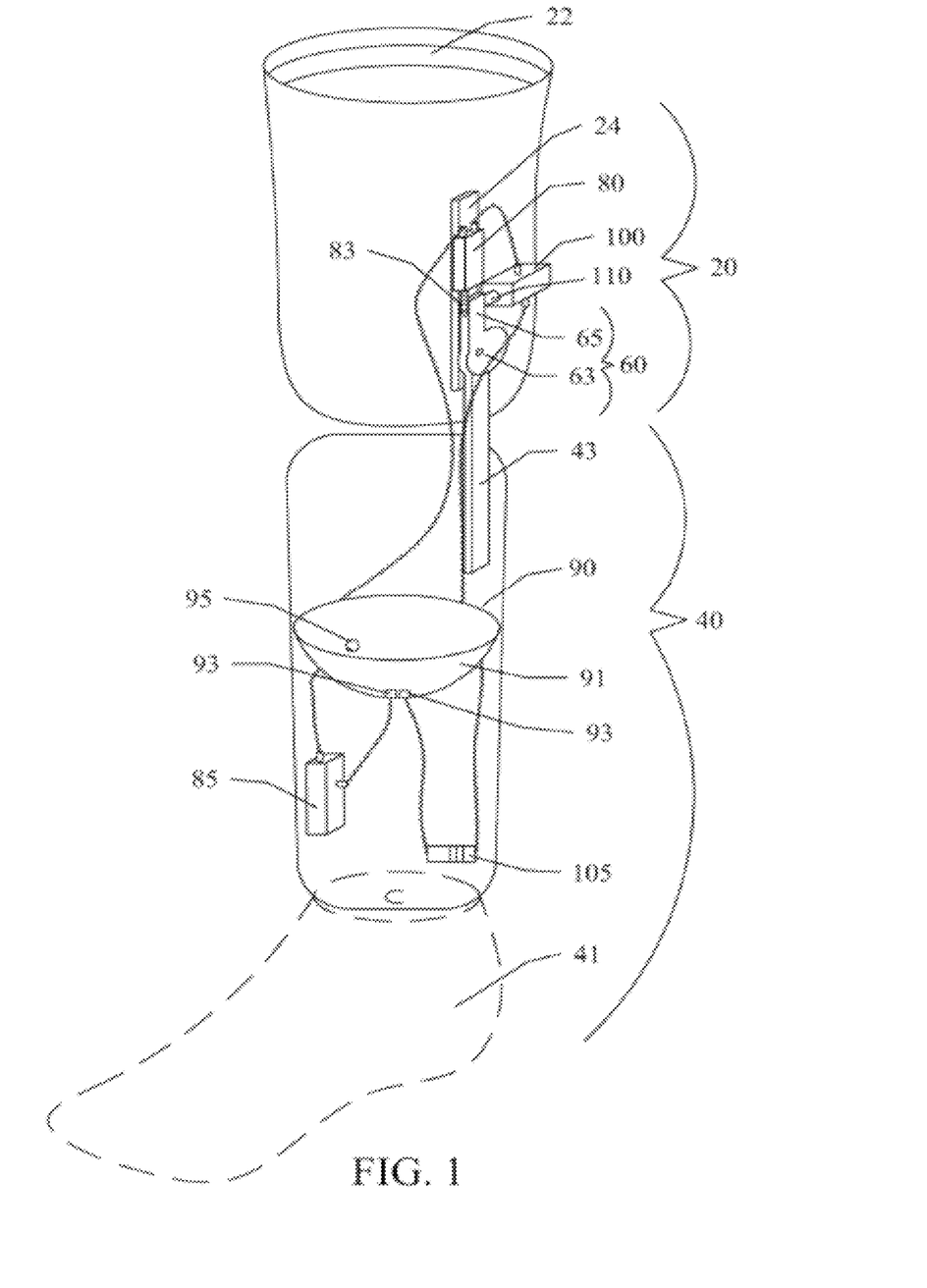
FIG. 1 is an illustration of one embodiment of the prosthetic knee system of the subject invention. This embodiment utilizes a "tilt-switch" mechanism to automatically lock the knee elements.
Figure 5:
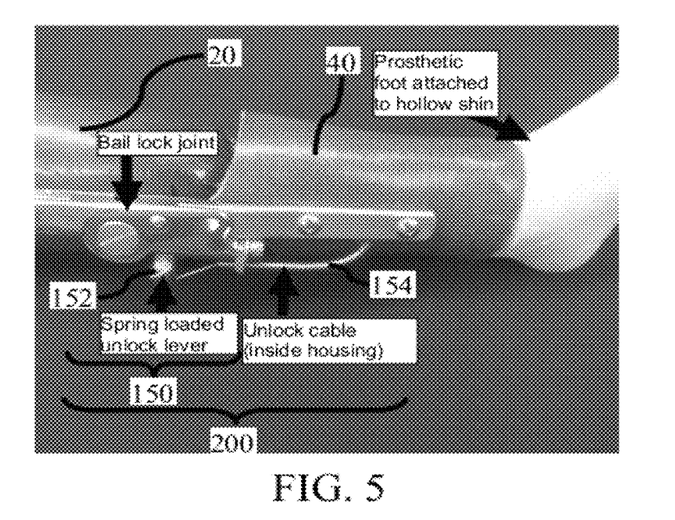
FIG. 5 is a photograph of a prototype for an alternative embodiment of the prosthetic knee system of the subject invention. Shown are upper and lower leg elements with an attached spring-loaded bail lock system controlled by a motorized cable.

FIG. 1 illustrates one embodiment of the subject invention that utilizes a single-axis articulating joint 60. In this embodiment, the rotating element 63 permits motion of the lower leg element in the backward direction, but forward motion is prevented by a stop flange 65, fixedly attached to the lower rod 43 that abuts against a pressure switch 100 when the lower leg element is fully extended. FIG. 5 illustrates an embodiment utilizing a single-axis articulating joint 60, wherein the rotating element 63 is controlled by a mechanized bail lock mechanism.

Utilizing a free-knee prosthetic requires patients to learn the proper way to adjust their walking pattern and stance to avoid falling. This is because free-knee prosthetic devices usually do not have stance control; therefore, patients must use their own muscle control to remain stable when standing or walking. Some patients, such as pre-ambulatory pediatric patients, do not have sufficient muscle strength or control to properly handle standing and walking with a free-knee prosthetic device. To compensate for a lack of muscle control and to assist with standing and walking, patients oftentimes are initially fitted with a straight-leg prosthesis. But, these are usually unwieldy, cause a stiff, awkward gait and, in younger patients, can interfere with proper development. An alternative strategy, well-known in the art, is to employ a manual lock with free-knee prosthetic that can be utilized to hold the upper leg element and lower leg element in an extended position for walking. For older, or more experienced patients, a manual lock can be advantageous. But, for younger, pre-ambulatory, or inexperienced patients, it can be unreasonable to expect them to understand how to manipulate a manual lock and/or coordinate its use with learning to walk.

One embodiment of the subject invention utilizes a knee-lock 80 with a locking mechanism that, when engaged, controls motion of the lower leg element in the backward direction, thus effectively locking the lower leg element in a sufficiently extended position. In a further embodiment, the locking mechanism of the knee-lock 80 engages with the articulating joint 60 to restrict motion in the backward direction. In a still further embodiment, the locking mechanism engages with the stop flange 65 affixed to the articulating joint to restrict motion in the backward direction. In yet a further embodiment, the knee-lock is electrically controlled. In a specific embodiment, a battery 85 can be operably connected with, and used to power, the knee-lock. A person with skill in the art would be able to determine any of a variety of batteries or other energy sources that would be useful with the embodiments of the subject invention. Any and all such variations are considered to be within the scope of the subject disclosure.

There are a variety of locking mechanisms 30 that can be utilized with a knee-lock to prevent or restrict motion of the stop flange 65. For example, various types of electro-magnets can be utilized with electric locks to restrict motion of the stop flange 65 or the lower leg rod 43.

One embodiment, shown, for example, in FIG. 1, employs a retractable pin 83 that, when extended, interferes with the motion of the stop flange 65, preventing it from moving forward as the lower rod 43, to which it connects, tries to move backwards. In this embodiment, when the electric lock 80 receives an appropriate signal, the retractable pin 83 is extended from the electric lock to engage with the stop flange 65, as shown in FIG. 1, or it can be retracted by the electric lock to allow full motion to the stop flange, and, thus, the lower leg element.

In an alternative embodiment, the motion of the articulating joint 60 is controlled by activation of a bail or French lock mechanism 150, generally shown, for example, in FIG. 5. Bail locks are known to those with skill in the art and usually employ a horizontal semi-circular lever 152 located behind the knee-joint. Activating the lever disengages the locking mechanism allowing the articulating joint 60 to rotate. The lever can also be spring-biased 153, so that when the articulating joint is in the correct position (i.e., when the upper and lower rods are sufficiently aligned), the lock automatically engages to restrict motion. Usually the patient is able to activate the lever and disengage the lock by backing up to a chair or other seat and using it to move the lever, allowing the articulating joint to bend for sitting down. When a cord, cable, or other elongate flexible member is attached to the lever to control the locking mechanism more distally, it is usually referred to then as a Swiss lock system.

Figure 6:
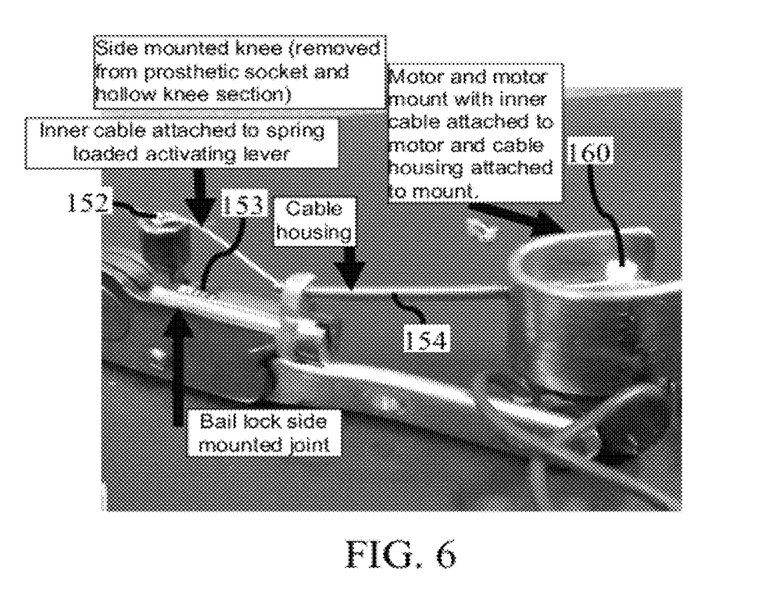
FIG. 6 is a photograph of the working components of the spring-loaded bail lock of the embodiment shown in FIG. 5.
Figure 7:
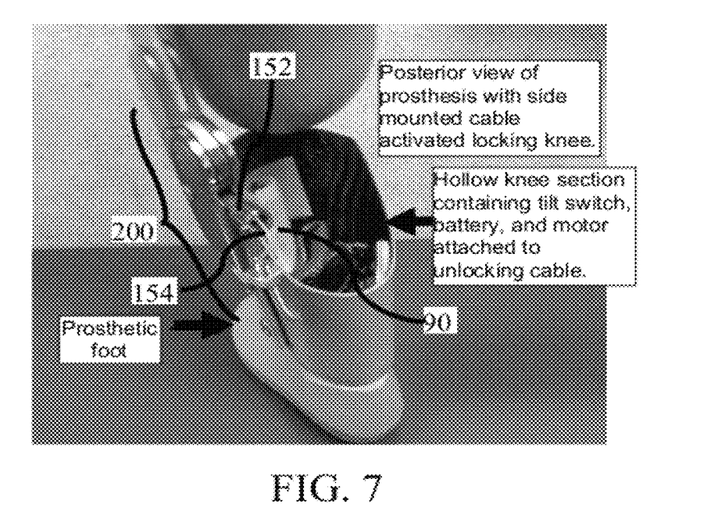
FIG. 7 is a photograph of the posterior side of the alternative embodiment. It can be seen that the electrical components of the locking system can be stored in the lower leg element to present a more streamlined appearance to the prosthesis.

In one embodiment of the subject invention, the articulating joint 60 is controlled by an electrical Swiss lock system 200, shown for example, in FIGS. 5-8. In this embodiment, the cord 154 of a Swiss lock, as described above, is operatively attached to an actuator 156. In a specific embodiment, the actuator is operatively connected to an electric motor 160, such as that shown, for example, in FIG. 8. In a further embodiment, the electric motor is operatively connected to and powered by a battery 162, for example, as further shown, in FIG. 8. In a specific embodiment, the function of the motor 160 is to cause the actuator 156 to pull, twist, or otherwise shorten the cord 154, so as to cause the lever 152, attached thereto, to disengage from the articulating joint 60, allowing it to rotate. FIG. 6 illustrates an example of the connection between the lever 152, the cord 154, the actuator 156, and the motor 160 of the mechanized Swiss lock system. A person with skill in the art having benefit of the subject disclosure can determine any of a variety of electric locks and other types of locking mechanisms that can be utilized to restrict or control the motion of the lower leg element. Such variations are contemplated to be within the scope of the subject invention.

As mentioned above, some patients may not be able to manually trigger a locking mechanism at the appropriate time for walking or standing. One advantage of embodiments of the subject invention is the ability of the electric lock or motor to be triggered automatically, or remotely. This can eliminate the need to manually or physically control the locking mechanism, making it usable by more patients, such as, for example, pre-ambulatory, pediatric patients learning to walk.

Figure 8:
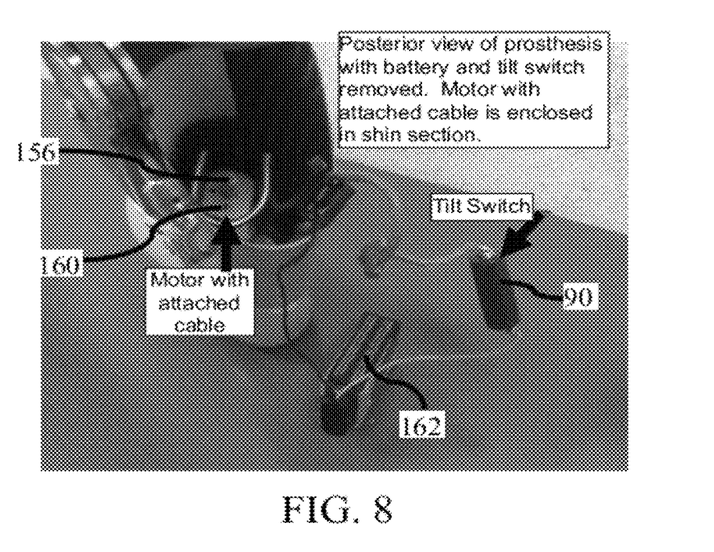
FIG. 8 is a photograph of the embodiment shown in FIG. 7 with the battery and tilt switch removed, showing the motor positioned within the lower leg element.

In one embodiment, an enclosed "tilt-switch" 90 can be used in combination with an knee-lock 80 to provide a fully automatic motion-controlled locking mechanism. A tilt-switch is, in general, a motion-controlled electrical switch. FIG. 1 illustrates an example of a tilt-switch using a shallow dish-shaped switch container 91 having at least two contacts 93 at, or near, the bottom thereof FIG. 8 illustrates an embodiment that utilizes an alternative type of tilt-switch, wherein electrical connection is made when the switch is rotated or turned horizontally. Further, alternative embodiments can utilize tilt-switches with multiple contacts. In one embodiment, an electrical connection made between the two contacts 93 activates the locking or unlocking mechanism to, for example, extend a retractable pin 83 or disengage a Swiss lock lever, as described above. To facilitate the electrical connection between the contacts, an appropriate motion-controlled connector 95 can be enclosed in the tilt-switch 90. A motion-controlled connector 95 can include, by way of non-limiting examples, any appropriately sized and type of electrically-conducting bearing or a sufficient quantity of room temperature liquid mercury, or other electrically conducting apparatus or substance, capable of spanning the distance between or otherwise connecting the at least two contacts.

In one embodiment, the tilt-switch and other components of the knee-lock can be located in the lower leg element. For example, with the Swiss-lock system, the motor 156, battery 162, tilt-switch 90, and most associated components can be stored within the lower leg element, as seen, for example, in FIG. 7. Advantageously, this can present a more stream-lined appearance to the prosthetic. FIG. 1 shows an embodiment having a tilt-switch 90 located in the lower leg element 40, at or near the "shin" area. In an alternative embodiment, the tilt-switch is located in the upper leg element 20. FIG. 1 also shows an embodiment of a tilt-switch where the switch container 91 has a relatively uniform shape. But, alternative embodiments can utilize switch containers 91 having different or variable curvatures, slopes, or shapes. Such shapes can conform to the outward shape and/or appearance of the prosthesis, or, in some instances, control the motion of the gravity-controlled connector 95. There are a variety of tilt switches known in the art that can, at the appropriate moment of motion, activate the locking or unlocking mechanism. The selection of an appropriate tilt-switch or similarly functioning mechanism is within the competence of those skilled in the art, as are the dimensions, configuration and location for the intended purpose disclosed herein.

In use, a patient wearing a prosthesis of the subject invention can bring himself to a standing position, such that the lower leg element 40 is extended and sufficiently vertically-aligned with the upper leg element 20. In one embodiment, upon reaching this alignment, the motion-controlled connector 95 will be in a position to make an electrical connection between the at least two contacts 93. When the connection is made, a signal is sent to the locking mechanism which will cause it to lock or unlock the articulating joint. In one embodiment, the signal causes the knee-lock 80 to extend a retractable pin 83 to prevent movement of the stop flange 65 and, thus, limit the backward motion of the lower leg element 40. In another embodiment, the signal activates a motor 156 to pull the cord 154 of a Swiss lock system releasing the locking lever 52 and allowing the articulating joint 60 to bend.

Further, when a patient desires to sit or for other reasons to disengage the lock mechanism, they can raise the prosthesis to a particular angle, or move it generally horizontally or to a position sufficiently non-vertically aligned, or otherwise move it appropriately. In one embodiment, utilizing an electric lock 80 with a retractable pin 83 this action will cause the motion-controlled connector 95 to disconnect from one or more of the contacts. This will break the electrical connection and retract the retractable pin 83. In the alternative embodiment, utilizing a Swiss lock system 200, raising the prosthesis, or positioning it sufficiently horizontal, will cause the tilt-switch connector 95 to make a connection between the two or more contacts, activating the motor, causing the cord 154 to pull the lever 152 to disengage the lock.

In some situations, it is desirable for the knee-lock 80 to have an external control, so that it is not automatic, as described in the above-embodiments. For example, pediatric patients during normal crawling or playing, or even when being picked up by a caregiver, could accidentally cause the locking mechanism to engage. It can even be helpful in some training situations for the locking mechanism to remain unengaged, even when the upper leg element is aligned with the lower leg element. Thus, having an knee-lock that can be remotely controlled by a patient, prosthetist, doctor, or caregiver can be helpful in some situations.

Figure 2:
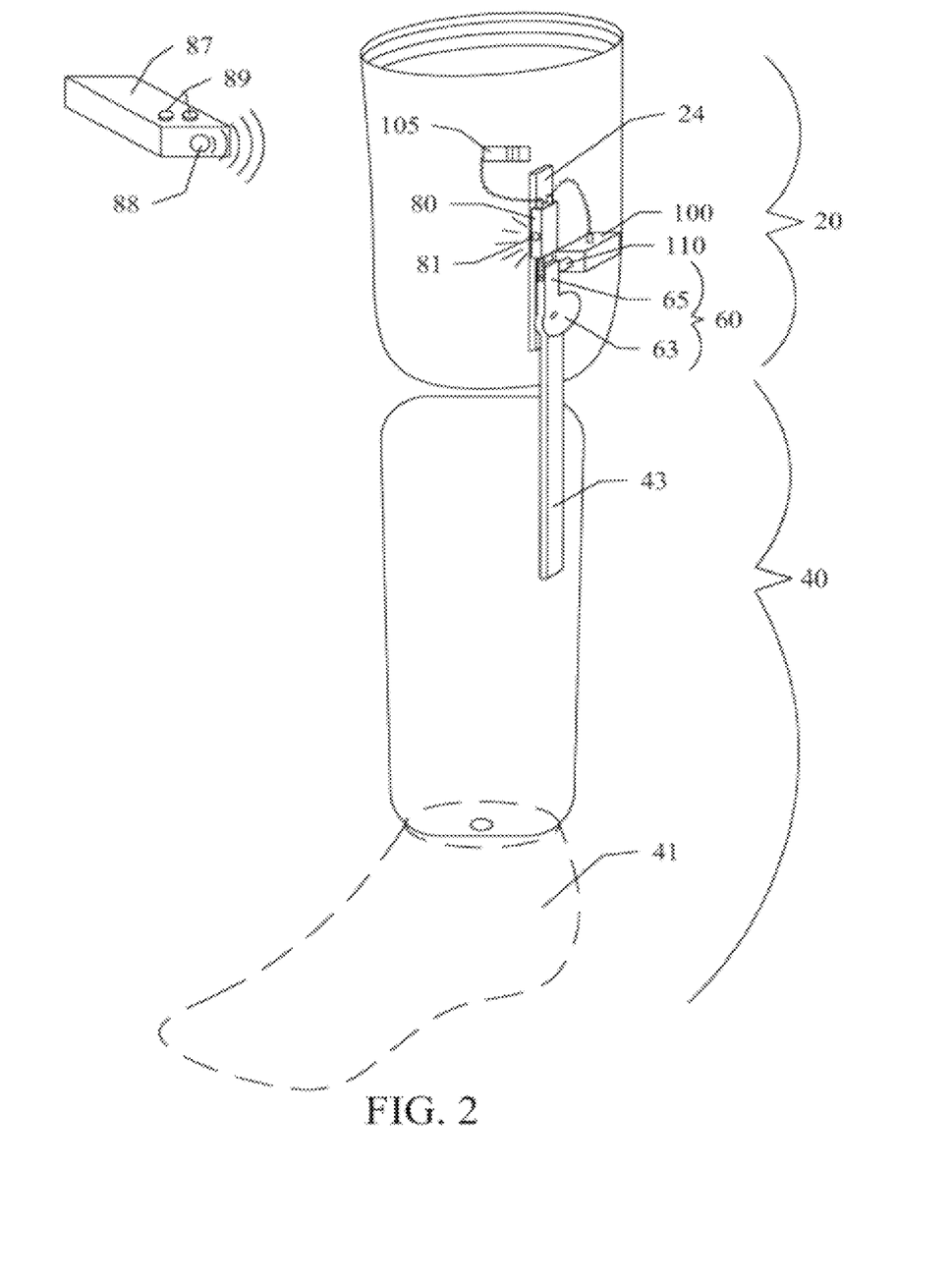
FIG. 2 is an illustration of another embodiment of the prosthetic knee system of the subject invention. This embodiment utilizes an external control mechanism to lock the knee elements.
Figure 3:
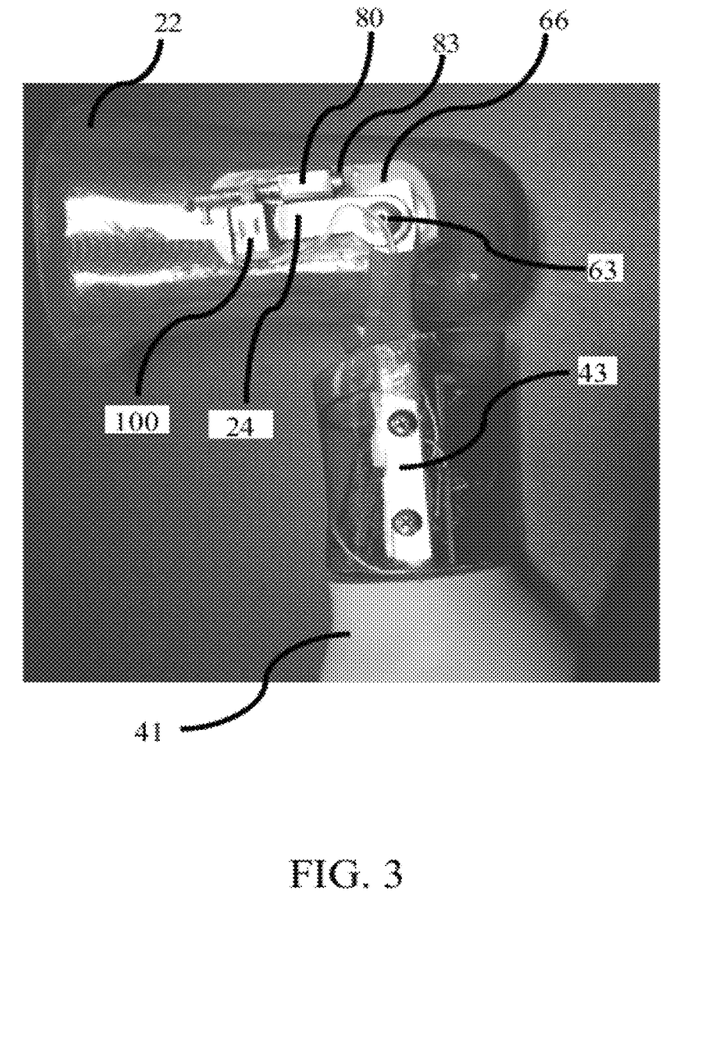
FIG. 3 is a photograph of a prototype of an embodiment of the prosthetic knee system of the subject invention. Shown is the articulation of the upper and lower leg elements.
Figure 4:
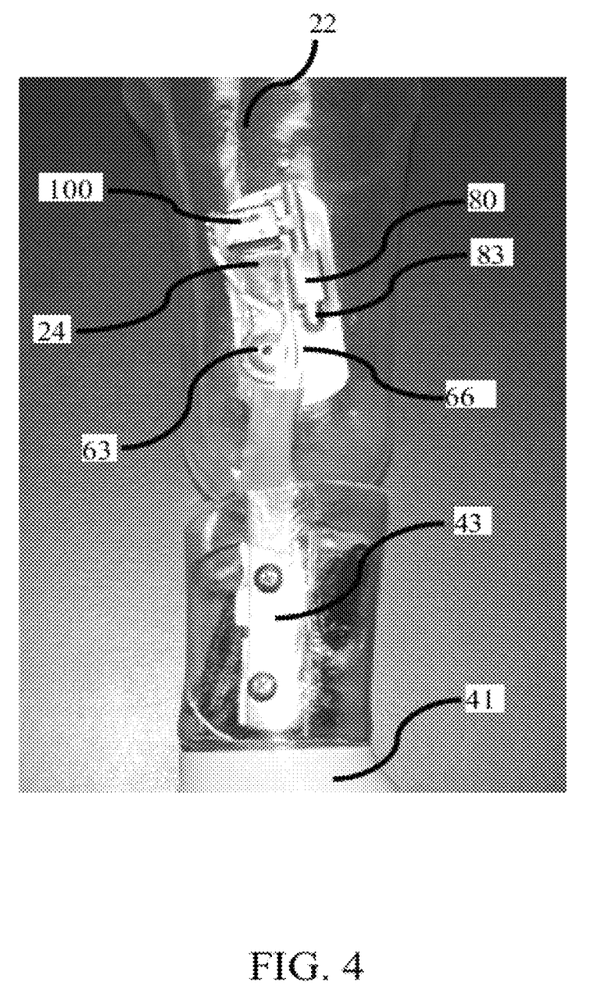
FIG. 4 is a photograph of the prototype in FIG. 3 showing the extension and alignment of the upper and lower leg elements.

In one embodiment, a knee-lock 80 as described above is controlled by a remote device, such as, for example, a fob having one or more buttons or switches. In a particular embodiment, the knee-lock is controlled by a wireless remote device 87. FIG. 2 illustrates an embodiment of an knee-lock 80 with a radio frequency receiver 81. Upon receiving an appropriate signal from a transmitter 88 from the controls 89 of a remote control device 87, the locking mechanism, such as a retractable pin 83 described above, responds appropriately, e.g., either extending or retracting the retractable pin. Remote control devices and actuators used therewith are well-known to those with skill in the art. Any and all variations other than those described herein are contemplated to be within the scope of the subject invention, to the extent that they are not inconsistent with the teachings of the subject disclosure.

Under certain circumstances, it may be possible for the knee-lock to be triggered accidentally causing the locking mechanism, such as a retractable pin 83, to engage with the stop flange 65 at an inappropriate time. For example, when a patient is in a sitting position, the motion-controlled connector in a tilt-switch 90 can automatically settle at the bottom of the switch-container 91, which, in one embodiment discussed above, makes a connection between the at least two switches 93 triggering the locking mechanism. In this embodiment, triggering the locking mechanism causes the retractable pin to extend, making it impossible for the upper and lower leg elements to align when the patient tries to stand. Additionally, in an embodiment utilizing a remote controlled locking mechanism; it is possible for the controls 89 to be accidentally touched or activated, which can also inappropriately affect the locking mechanism. Thus, in one embodiment, the locking mechanism has at least one safety mechanism that reduces or prevents undesirable activation.

In one embodiment, a pressure switch 100 is in operable communication with the locking mechanism. In a further embodiment, the pressure switch 100 is positioned such that contact with the stop flange 65 or other section of the lower leg rod 43 controls the action of the locking mechanism. In a particular embodiment, the pressure switch 100 is positioned in the back of the stop flange, as shown, for example, in FIGS. 1 and 2, whereby movement of the lower rod into vertical alignment with the upper rod causes the stop flange 65, as it rotates, to come into operable connection with the activating mechanism 110 of the pressure switch. Activation of the pressure switch can subsequently trigger the locking mechanism to restrict backward movement of the lower leg element 40.

It will be understood by those with skill in the art that a variety of other arrangements of the mechanism disclosed in the subject invention for sensing and restricting the motion of the rods can be used.

It is possible that, when utilizing a prosthetic device of the subject invention, situations may arise where it is necessary or desirable to temporarily disable the device. In some situations it may be desirable for the disabled device to continue to function as a free knee prosthetic. In other situations, a straight knee disabled device is more useful.

In a further embodiment, the prosthetic devices described herein have at least one on/off switch 105 that can temporarily disable the prosthetic device. In one embodiment, the on/off switch disables the device regardless of the positions of the upper and lower rods. Thus, if the rods are aligned and locked when the switch 105 is turned off, they will remain so until the switch 105 is turned on. Conversely, if the rods are articulated when the switch is turned off, the prosthetic will function as a free-knee device until the switch is turned on. Alternatively, the on/off switch 105 can be activated only when the upper and lower rods are in a pre-determined position. For example, the on/off switch can only be activated when the upper and lower rods are aligned. Substitution of other "on/off" switch arrangements other than those specifically exemplified herein are also contemplated to be within the scope of the subject invention.

The prosthetic devices disclosed herein provide advantages over currently known free-knee leg prosthetics. The locking external joint mechanisms are particularly suited for long residual limbs where a traditional prosthetic knee cannot be mounted at the equivalent height of the contra-lateral knee center, but they are also useful for short trans-femoral residual limbs. The advantages include increased mobility of a free-knee prosthetic system and the stability of a stiff or straight-leg prosthetic for walking and standing. While useful to many types of patients, they can be especially helpful for pre-ambulatory pediatric patients learning to walk for the first time.

All patents, patent applications, provisional applications, and publications referred to or cited herein are incorporated by reference in their entirety, including all figures and tables, to the extent they are not inconsistent with the explicit teachings of this specification.

The examples and embodiments described herein are for illustrative purposes only and that various modifications or changes in light thereof will be suggested to persons skilled in the art and are to be included within the spirit and purview of this application.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. Further, when a particular feature, structure, or characteristic is described in connection with any embodiment, it is within the purview of one skilled in the art to affect such feature, structure, or characteristic in connection with other embodiments.

The invention has been described herein in considerable detail, in order to comply with the Patent Statutes and to provide those skilled in the art with information needed to apply the novel principles, and to construct and use such specialized components as required. However, the invention can be carried out by different equipment and devices, and that various modifications, both as to equipment details and operating procedures can be effected without departing from the scope of the invention. Further, although the present invention has been described with reference to specific details of certain embodiments thereof, it is not intended that such details should be regarded as limitations upon the scope of the invention except as and to the extent that they are included in the accompanying claims.

I claim:

1. A prosthetic device comprising:
   an upper leg element;
   a lower leg element;
   a single-axis articulating joint fixedly connected between the upper and lower leg elements;
   an electric knee-lock capable of controlling the motion of the articulating joint; and
   a gravity-activated tilt-switch operably connected to the knee-lock, such that, when activated the tilt-switch transmits an electrical signal to the knee-lock to control the motion of the articulating joint.

2. The prosthetic device, according to claim 1, wherein the tilt-switch is activated by the position of the lower leg element.

3. The prosthetic device, according to claim 2, wherein the knee-lock is disengaged when the lower leg element is moved out of vertical alignment with the upper leg element.

4. The prosthetic device, according to claim 3, wherein the knee-lock comprises a retractable pin that operably connects with a stop flange attached to the articulating joint to control the motion of the articulating joint.

5. The prosthetic device, according to claim 4, further comprising a pressure switch in operable communication with the knee-lock.

6. The prosthetic device, according to claim 5, further comprising a battery in operable communication with the knee-lock.

7. The prosthetic device, according to claim 1, wherein the knee-lock comprises a Swiss lock system having:
- a spring-biased lever operably engaged with the articulating joint;
- an elongate flexible member having a first end attached to the lever; and
- a motor with an actuator operably attached to a second end of the elongate flexible member, such that activation of the motor causes the actuator to act on the elongate flexible member to disengage the lever from the articulating joint.

8. The prosthetic device, according to claim 7, wherein the spring-biased lever automatically locks the articulating joint when the upper leg element and the lower leg element are generally vertically-aligned.

9. The prosthetic device, according to claim 8, wherein the motor is battery operated.

10. The prosthetic device, according to claim 9, further comprising an on/off switch.

11. The prosthetic device, according to claim 10, wherein the on/off switch disables the articulating joint regardless of the position of the upper leg element and lower leg element.

12. The prosthetic device, according to claim 10, wherein the on/off switch disables the articulating joint only when the upper leg element and lower leg element are in a pre-determined alignment.

13. The prosthetic device, according to claim 1, wherein the tilt-switch is activated by remote control.

14. The prosthetic device, according to claim 13, wherein the remote control is in wireless communication with the knee-lock.

15. A kit comprising:
- a prosthetic device comprising,
  - an upper leg element;
  - a lower leg element;
  - a single-axis articulating joint fixedly connected between the upper and lower leg elements;
  - an electric knee-lock capable of controlling the motion of the articulating joint; and
  - a gravity-activated tilt-switch operably connected to the knee-lock, such that, when activated the tilt-switch transmits an electrical signal to the knee-lock to control the motion of the articulating joint;
- at least one battery; and
- a remote control operably connected to the knee-lock.

* * * * *

UNITED STATES PATENT AND TRADEMARK OFFICE
CERTIFICATE OF CORRECTION

| | | |
|---|---|---|
| PATENT NO. | : 8,192,501 B2 | |
| APPLICATION NO. | : 12/567301 | |
| DATED | : June 5, 2012 | |
| INVENTOR(S) | : Peter Kapelke | |

It is certified that error appears in the above-identified patent and that said Letters Patent is hereby corrected as shown below:

In the Specifications:

Column 4,
Line 47, ""For example, various types of electro-magnets can be utilized with electric locks to restrict motion of the stop flange or the lower leg rod.
One embodiment, shown, for example," should read
--For example, various types of electro-magnets can be utilized with electric locks to restrict motion of the stop flange or the lower leg rod. One embodiment, shown, for example,--

Column 5,
Line 42, "thereof FIG. 8" should read --thereof. Figure 8--

Signed and Sealed this
Thirty-first Day of July, 2012

David J. Kappos
*Director of the United States Patent and Trademark Office*